United States Patent [19]

Pruitt

[11] Patent Number: 4,578,035
[45] Date of Patent: Mar. 25, 1986

[54] DENTAL WEDGE

[76] Inventor: Darrell K. Pruitt, 2817 Stark, Suite A, Fort Worth, Tex. 76112

[21] Appl. No.: 735,949

[22] Filed: May 20, 1985

[51] Int. Cl.[4] ............................................. A61C 7/00
[52] U.S. Cl. .................................................. 433/149
[58] Field of Search ...................................... 433/149

[56] References Cited

U.S. PATENT DOCUMENTS

| 351,065 | 10/1886 | Miller | 433/149 |
| 2,891,313 | 6/1959 | Crowley | 433/149 |
| 4,259,070 | 3/1981 | Soelberg et al. | 433/149 |

Primary Examiner—Robert Peshock
Attorney, Agent, or Firm—Arthur F. Zobal

[57] ABSTRACT

In one embodiment the Dental Wedge is formed by two flexible members defined as a gingival member and an occlusal member. The gingival member is C-shaped between its ends and generally triangular shaped in cross section. It has an outer side which gradually increases in width from a pointed end to a wider end. The occlusal member is curved and is also generally triangular shaped in cross section. Connectors are provided for connecting the two ends of the two members together to form a closed loop wedge. The gingival member may be inserted partially through the gingival embrasure of two adjacent teeth from its pointed end with its outer side facing the gum. One end of the occlusal member then may be connected to the pointed end of the gingival member and the occlusal member next stretched across and fitted within the occlusal embrasure of the two adjacent teeth and its other end connected to the other end of the gingival member to form a closed loop wedge which fills the gingival, buccal, lingual and occlusal embrasures between the two adjacent teeth.

In another embodiment, the Dental Wedge is formed by a single curved flexible member shaped to function in the same manner as the two member wedge.

18 Claims, 25 Drawing Figures

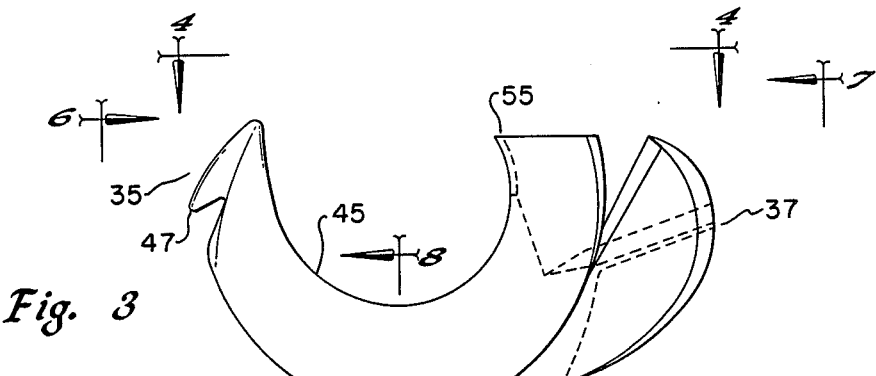
Fig. 3
Fig. 4
Fig. 8
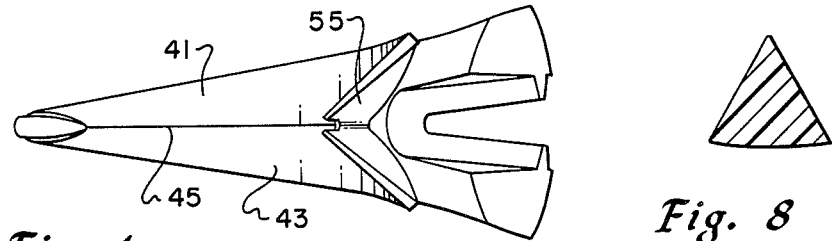
Fig. 5
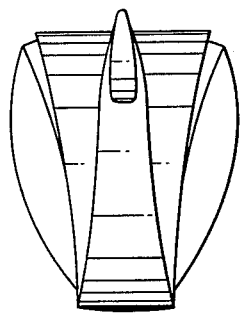
Fig. 6
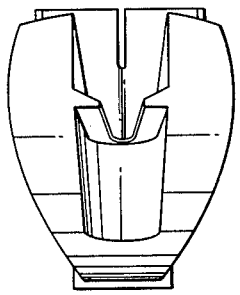
Fig. 7

4,578,035

DENTAL WEDGE

FIELD OF THE INVENTION

A wedge for use in restoring teeth.

BACKGROUND OF THE INVENTION

For many years, cavities in teeth have been filled with amalgam which is an alloy of mercury and other metals. The amalgam has a thick consistency which enables a dentist to pack it into a cavity preparation and to establish contours with a matrix band through compression before the amalgam hardens. In addition, the amalgam is relatively easy to trim before the final set. Recently new plastic materials have been developed for restoration purposes. These materials are formed of a base and a catalyst which react to form a very hard material which is difficult to trim. Moreover, these materials do not have the consistency to be compressed, for example, with the conventional matrix band, into a cavity preparation to form the desired contours. In addition, they set up very rapidly, thereby enhancing the difficulty of establishing the desired contours by compression. The conventional wooden wedges and cellophane strips have been used with these materials to establish the sought after contours, however the results are not satisfactory in all cases.

U.S. Pat. Nos. 351065, 388620, 625888, 701799, 1133379, 1935481, 2629930, 2891313 and 3108377 disclose different types of dental matrices and wedges, however, they are not satisfactory for use with the new plastic materials.

SUMMARY OF THE INVENTION

It is an object of the invention to provide an apparatus which can be used with the new plastic materials to effectively establish the desired dental contours before the material is inserted into the cavity preparation such that trimming is minimized. The apparatus is shaped such that it will intimately fill the gingival, buccal, lingual, and occlusal embrasures between two adjacent teeth.

In one embodiment, the apparatus comprises two flexible members, one being defined as a gingival member and the other being defined as an occlusal member. The gingival member is C-shaped and generally triangular in cross section. It has an outer side and two other sides which extend from opposite edges of the gingival side to a pointed edge where they meet. The occlusal member also is generally triangular in shape. It has an outer side and two other sides which extend from opposite edges of the outer side to a pointed edge where they meet. Means is provided for connecting the two ends of the gingival member to the two ends of the occlusal member such that a closed loop wedge is formed by the gingival and occlusal members with their pointed edges defining a central opening. The gingival member is adapted to be inserted partially through the gingival embrasure of two adjacent teeth from its smaller end with its outer side facing the gum whereby the pointed edge of the occlusal member may be fitted within the occlusal embrasure of the two adjacent teeth and the two ends of the gingival member connected to the two ends of the occlusal member to form a closed loop wedge which intimately fills the gingival, buccal, lingual, and occlusal embrasures between the two adjacent teeth.

In another embodiment, the apparatus comprises a single curved flexible member having a gingival portion and an occlusal portion. The occlusal portion extends from one end to an intermediate position along the length of the member and the gingival portion extends from about the intermediate position to the other end of the member. The member is generally triangular in cross section between its two ends. The member has an outer side and two other sides which extend from opposite edges of the outer side to a pointed edge where they meet each other. Means is provided for connecting the two ends of the member together to form a closed loop wedge which with the pointed edge defining a central opening. The member is adapted to be inserted partially through the gingival embrasure of two adjacent teeth, from said one end with its outer side facing the gum, to a position where its gingival portion is within the gingival embrasure, whereby the occlusal portion including its pointed edge may be fitted within the occlusal embrasure of the two adjacent teeth and the two ends of the member connected together to form a closed loop wedge which intimately fills the gingival, buccal, lingual and occlusal embrasures between the two adjacent teeth.

BRIEF DESCRIPTION OF THE DRAWINGS

FIG. 3 is a side view of the gingival member of the wedge.

FIG. 4 is a view of the member of FIG. 3 as seen from lines 4—4 thereof.

FIG. 5 is a view of the member of FIG. 3 as seen from lines 5—5 thereof.

FIG. 6 is a view of the member of FIG. 3 as seen from lines 6—6 thereof.

FIG. 7 is a view of the member of FIG. 3 as seen from lines 7—7 thereof.

FIG. 8 is a cross section of the member of FIG. 3 as seen from lines 8—8 thereof.

DETAILED DESCRIPTION OF THE PREFERRED EMBODIMENTS

Figure 1:
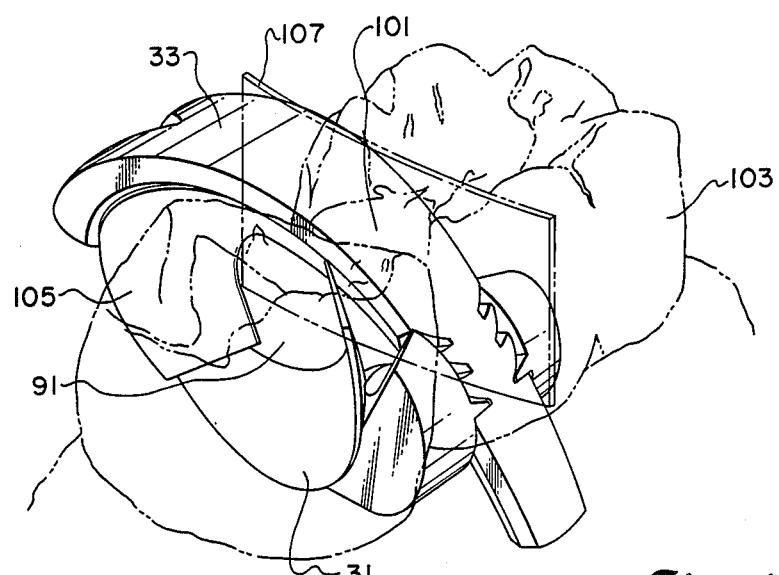
FIG. 1 illustrates one embodiment of the dental wedge of the invention in place between two adjacent teeth. In this embodiment the wedge is formed by two separate members defined as a gingival member and occlusal member.
Figure 2:
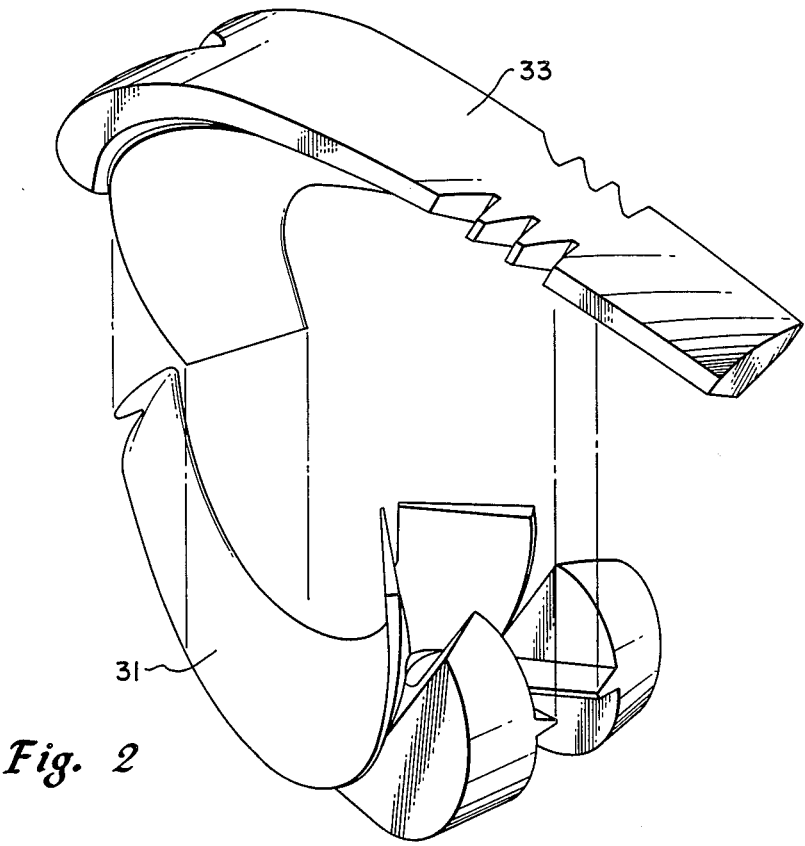
FIG. 2 is an exploded view of the gingival and occlusal members of the wedge in FIGS. 1 and 2.
Figure 9:
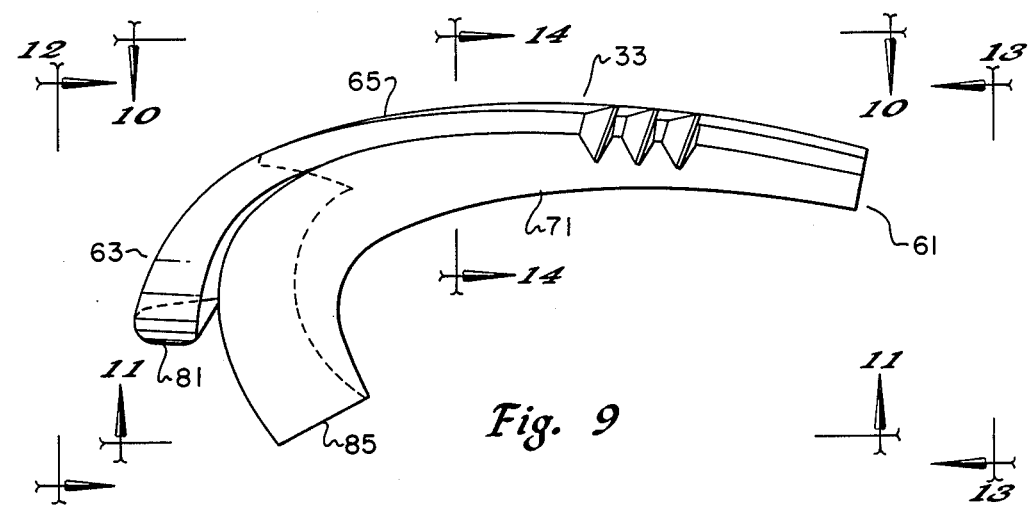
FIG. 9 is a side view of the occlusal member of the wedge of FIGS. 1 and 2.
Figure 10:
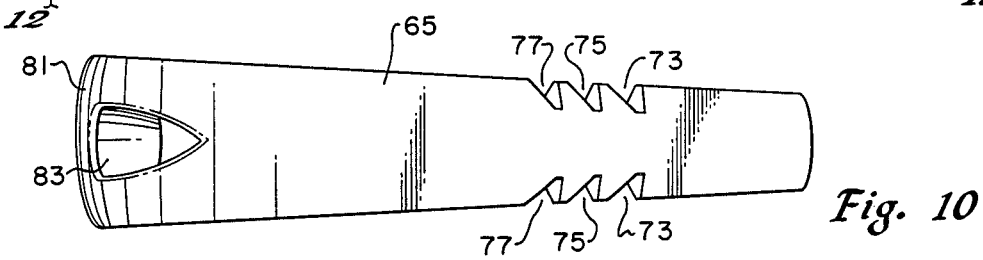
FIG. 10 in a view of the member of FIG. 9 as seen from lines 10—10 thereof.
Figure 11:
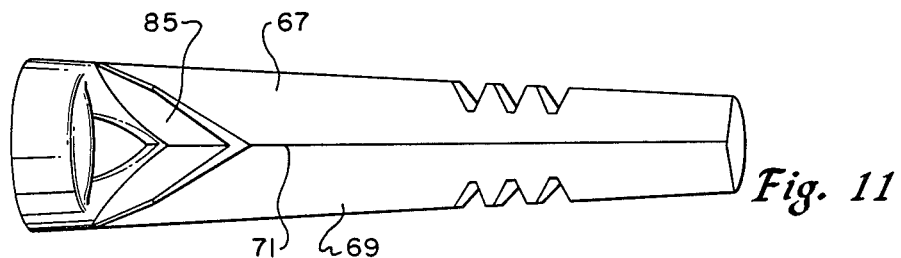
FIG. 11 is a view of the member of FIG. 9 as seen from lines 11—11 thereof.
Figure 14:
FIG. 14 is a cross section of the member of FIG. 9 as seen from lines 14—14 thereof.
Figure 12:
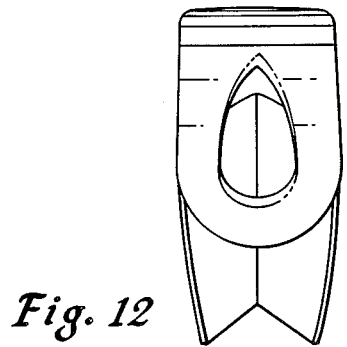
FIG. 12 is a view of the member of FIG. 9 as seen from lines 12—12 thereof.
Figure 13:
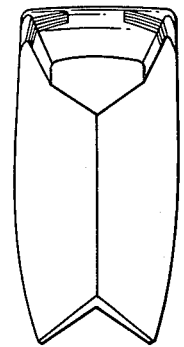
FIG. 13 is a view of the member of FIG. 9 as seen from lines 13—13 thereof.
Figure 15:
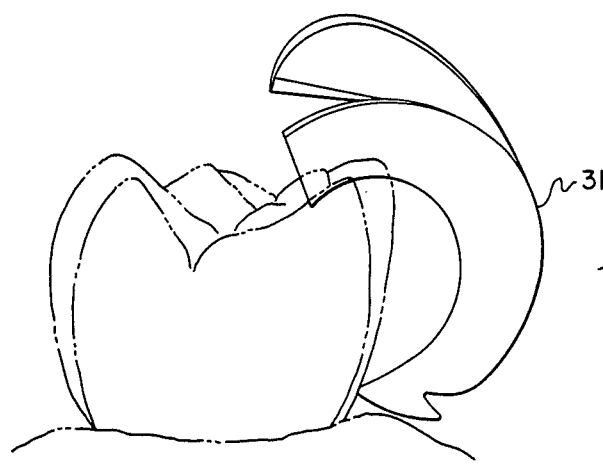
FIG. 15 illustrates the pointed end of the gingival member being inserted into the gingival embrasure between two adjacent teeth.
Figure 16:
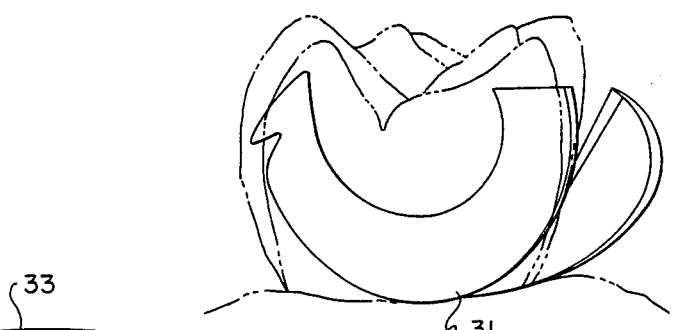
FIG. 16 illustrates the gingival member as located in the gingival embrasure of the two adjacent teeth.
Figure 17:
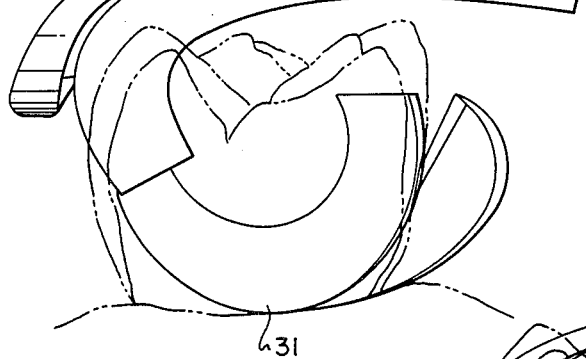
FIG. 17 illustrates the occlusal member being connected to one end of the gingival member when it is in place.

Referring now to the embodiment of FIGS. 1-18, the wedge or apparatus of the invention comprises two flexible members defined as a gingival member or base 31 and an occlusal member or strap 33. The members 31 and 33 both are compressable and stretchable and preferably are made of a suitable elastic material. As seen in FIGS. 1-8, the gingival member 31 has a pointed end 35 and a wide end 37 and is C-shaped between its two ends 35 and 37. It is also generally triangular in cross section between its ends 35 and 37. The gingival member has an outer side 39 and two inner sides 41 and 43 which extend from opposite edges of the outer side 39 to a pointed edge 45 where they meet each other. The outer side 39 gradually increases in width from the pointed end 35 toward the wide end 37. A hook 47 is formed at the pointed end 35 on the outer side 39. A V-shaped connector 49 compressing arms 49A and 49B is formed at end 37 and has two inwardly facing prongs or pointed edges 51 and 53. The two sides 41 and 43 at end 37 form a trough 55 which splits off and is separate from the V-shaped connector 49.

Referring to FIGS. 9-14, the occlusal member 33 has a narrow end 61 and a wide end 63 and is curved such that it is generally L-shaped between the ends 61 and 63. It has an outer side 65 and two inner sides 67 and 69 which extend from opposite edges of the outer side 65 to a pointed edge 71 where they meet each other. The outer side 65 gradually increases in width from the smaller end 61 toward the wider end 63. A plurality of pairs of notches 73, 75, and 77 are formed in opposite edges of the occlusal member near its narrow end 61. The notches extend inward from the outer side 65. A connector 81 with an eye or opening 83 is formed at the wider end 63. The two sides 67 and 69 at end 63 form a trough 85 which splits off and is separate from the connector 81.

Figure 18:
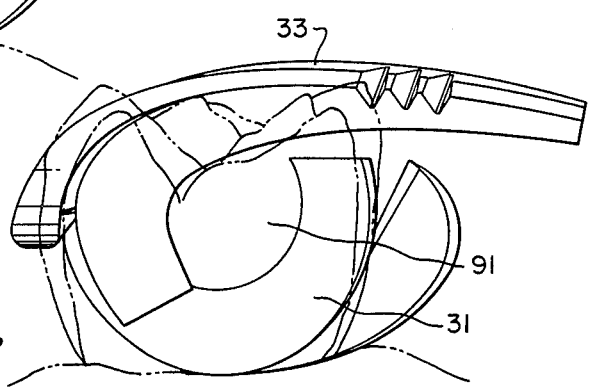
FIG. 18 illustrates the occlusal member being stretched through the occlusal embrasure between the two adjacent teeth for connecting its other end to the other end of the gingival member.
Figure 19:
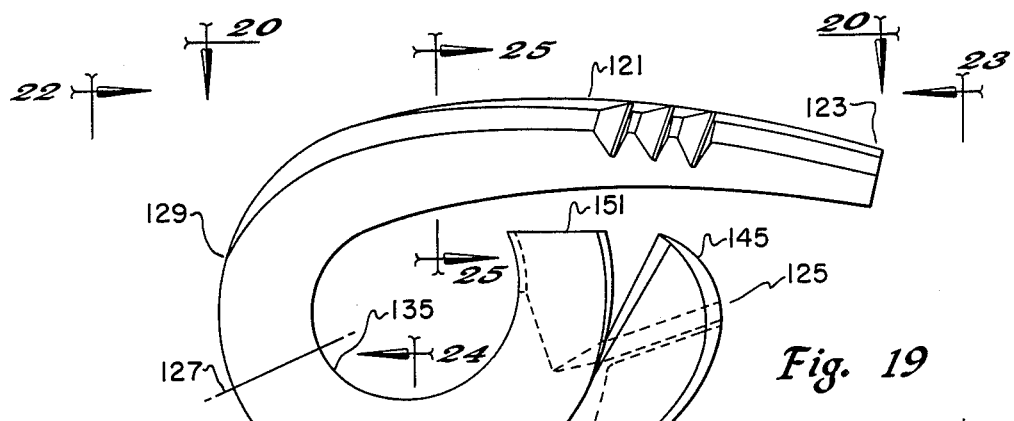
FIG. 19 is a side view of another embodiment of the wedge of the invention.
Figure 20:
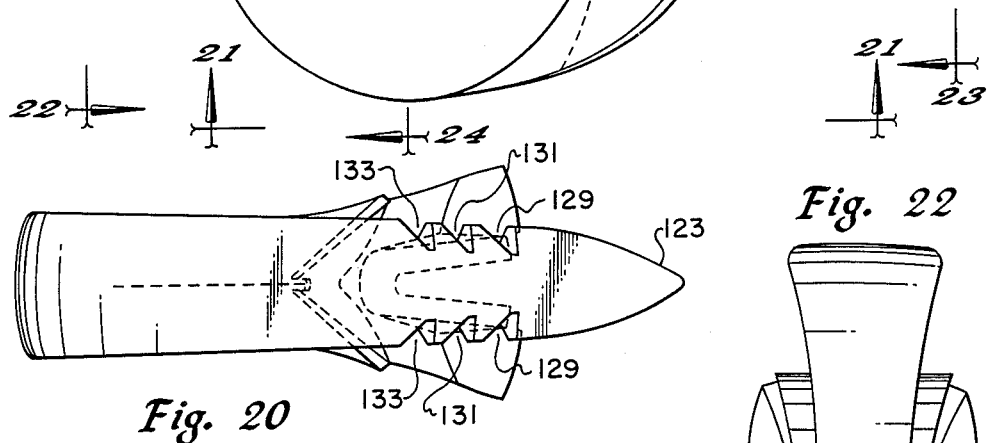
FIG. 20 is a view of the member of FIG. 19 as seen from lines 20—20 thereof.
Figure 22:
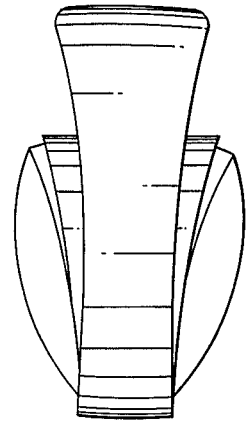
FIG. 22 is a view of the member of FIG. 19 as seen from lines 22—22 thereof.
Figure 21:
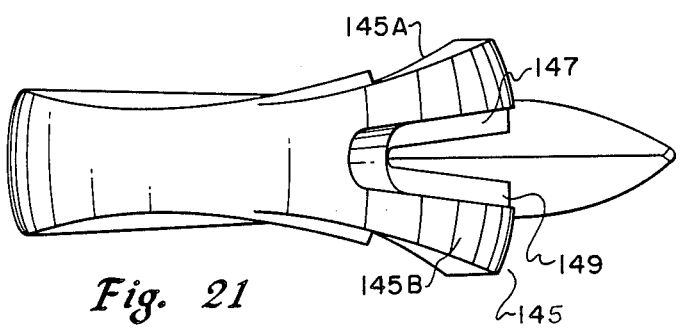
FIG. 21 is a view of the member of FIG. 19 as seen from lines 21—21 thereof.
Figure 24:
FIG. 24 is a cross section of the member of FIG. 19 as seen from lines 24—24 thereof.
Figure 25:
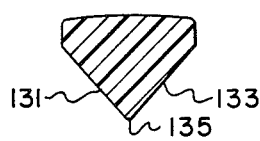
FIG. 25 is a cross section of the member of FIG. 19 as seen from lines 25—25 thereof.
Figure 23:
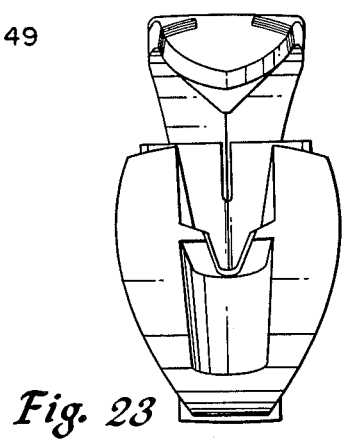
FIG. 23 is a view of the member of FIG. 19 as seen from lines 23—23 thereof.

The wide end 63 of the occlusal member is adapted to be connected to the pointed end 35 of the gingival member and the narrow end 61 of the occlusal member is adapted to be connected to the wide end 37 of the gingival member 31, such that a closed loop wedge is formed by the gingival and occlusal members with their pointed edges 45 and 71 defining a central opening as illustrated as 91 and which is nearly completed in FIG. 18.

The end 63 of the occlusal member 33 is connected to the pointed end 35 of the gingival member 31 by locating the pointed end 35 between the connector 81 and the trough 85 such that the hook 47 fits within the eye or opening 83. The end 61 of the occlusal member is connected to the end 37 of the gingival member by locating the end 61 at least partially between the sides of the trough 55 and between the two arms 49A and 49B of the V-shaped member 49 such that the prongs 51 and 53 will be located in one of the pairs of notches 73, 75, or 77.

The members 31 and 33 will be sized such that they can fit between the embrasures formed between adjacent teeth for restoration purposes. In FIG. 1, the wedge is shown employed to aid in restoring a cavity 101 prepared on the mesial of the mandibular right first molar 103 next to the mandibular right second bicuspid. In order to form the desired smooth contour with the aid of the wedge members 31 and 33, a pre-contoured thin sheet of plastic material 107 preferably will be located between the two teeth as shown in FIG. 1. The plastic sheet 107 may be transparent and have a thickness of 0.002 of an inch. Either from the lingual or buccal side, the gingival member 31 will be inserted partially through the gingival embrasure between the two teeth and the example shown in FIG. 1 between the plastic strip 107 and the mandibular right second biscuspid. The purpose of the plastic strip 107 is to obtain a smooth surface on the restoration. The gingival member is inserted partially through the gingival embrasure by pushing on its wide end 37 and also by pulling on its pointed end 35 after it has been inserted into the gingival embrasure. the gingival member is moved through the gingival embrasure until it reaches a position shown in FIG. 18. As the gingival member is pressed and inserted through the gingival embrasure with its outer surface 39 facing the gum, it will press apart and separate the adjacent teeth to allow for the re-establishment of interproximal contact. After the gingival member has been inserted partially through the gingival embrasure to the desired position, the occlusal member 33 is located such that the hook 47 fits within the eye or opening 83 of the connecting member 81 and then the occlusal member including its pointed edge 71 is stretched across and fitted within the occlusal embrasure to place the narrow end 61 within the trough 55 and between the arms 49A and 49B of the V-shaped connector 49 to the desired position wherein the prongs or sharp edges 51 and 53 fit within one of the pairs of slots 73, 75 or 77 depending on the size of the teeth. The purpose of the different pairs of notches 73, 75 and 77, is for adjustment purposes to allow the occlusal and gingival members to fit different size teeth. When the gingival and occlusal members 31 and 33 are inserted in place and attached together as shown in FIG. 1, their wedged shape surfaces defined by their pointed edges 45 and 71 and V-shaped inner sides 41, 43 and 67, 69 intimately fit within the gingival, buccal, lingual and occlusal embrasures between the two teeth to allow the desired contours for the cavity to be formed, whereby the cavity may be passively filled with a plastic material without the necessity of any further compression after the material is located within the cavity and also minimizing any subsequent trimming thereafter. Thus the gingival and occlusal members when inserted in place between two adjacent teeth interlock and establish the contour of the filling material circumferentially around the contact area. The occlusal member aids in establishing the height and contour of the restored marginal ridge. The result will be a class II (two surface) restoration which requires minimal post-set trimming and contouring. In the example shown, if a cavity exists on the distal side of the other tooth which in this instance is the mandibular right second bicuspid then a similar plastic strip may be located between this tooth and the wedge to form the desired contour. After the filling has sufficiently hardened, the wedge comprising the gingival and occlusal members 31 and 33 and the plastic strip 107 will be removed.

Referring to the embodiment of FIGS. 19-25, the wedge or apparatus comprises a single curved member 121 formed of the same material as the members 31 and 33. The wedging portions of the single member 121 are similar in shape as the wedging portions of the two members 31 and 33 when coupled together as shown in FIG. 18 and the member 121 is used for the same purpose as are members 31 and 33. Member 121 has a narrow pointed end 123 and a wide end 125 and can be defined as comprising an occlusal portion from an intermediate position beginning at about plane 127 to the end 123 and a gingival portion between plane 127 and the end 125. The curved member 121 has an outer side 129 which gradually increases in width from about plane 127 to the thicker end 125. It has two inner sides 131 and 133 which extend from opposite edges of outer side 129 to a pointed edge 135 where they meet each other. The gingival portion is generally triangular in shape in cross section between the plane 127 and its end 125 as seen in plane 24. Similarly the occlusal portion is generally triangular in cross section between the plane 127 and its end 123 as seen in plane 25. Near the end 123 is plurality of pairs of notches 129, 131 and 133 are formed. At the end 125 a V-shaped connector 145 comprising arms 145A and 145B is formed having inwardly facing prongs or pointed edges 147 and 149. At the end 125, the inner sides 131 and 133 form a trough 151 which splits off from the connector 145 and is separate therefrom.

The member 121 is used in a manner similar to that of the two members 31 and 33, to form a close loop wedge within the gingival, occlusal, lingual and buccal embrasures between two adjacent teeth. The member 121 is inserted in place by threading the pointed end 123 through the gingival embrasure with its outer surface 129 facing the gum, and then pushing and pulling the member 121 through the gingival embrasure until its gingival portion is located within the gingival embrasure at a position similar to that of member 31 as shown in FIG. 18. The occlusal portion including its pointed edge 135 then is stretched around and within the occlusal embrasure of the two adjacent teeth and its end 123 connected to the other end 125 by locating the end 123 partially within the trough 125 and between the arms 145A and 145B of the V-shaped connector 145 such that the prongs 147 and 149 fit within one of the pair of notches 129, 131 or 133. In using the wedge 121, a thin plastic strip 107 preferably also will be used as described in connection with the first embodiment.

In one embodiment, the members 31, 33 and 121 may be formed of vinyl polysiloxane. Preferably they will be used for restoration purposes of the posterior teeth.

I claim:

1. An apparatus for use for dental restoration, comprising:
   two flexible members, one being defined as a gingival member and the other being defined as an occlusal member,
   said gingival member having first and second ends and being generally C-shaped between said first and second ends,
   said gingival member having an outer side and two other sides which extend from opposite edges of said outer side to a pointed edge where they meet each other,
   said occlusal member having a first end and a second end,
   said occlusal member having an outer side and two other sides which extend from opposite edges of its outer side to a pointed edge where they meet each other,
   means for connecting said second end of said occlusal member to said first end of said gingival member and for connecting said first end of said occlusal member to said second end of said gingival member such that a closed loop wedge is formed by said gingival and occlusal members with their pointed edges defining a central opening,
   said gingival member being adapted to be inserted partially through the gingival embrasure of two adjacent teeth from its first end with its outer side facing the gum whereby the pointed edge of said occlusal member may be fitted within the occlusal embrasure of the two adjacent teeth and second end of said occlusal member connected to said first end of said gingival member and said first end of said occlusal member connected to said second end of said gingival member to form a closed loop wedge which fills the gingival, buccal, lingual, and occlusal embrasures between the two adjacent teeth.

2. The apparatus of claim 1, wherein:
   said outer side of said gingival member gradually increases in width from its first and toward its second end.

3. The apparatus of claim 1, wherein:
   said gingival member is generally triangular in shape in cross section between its first and second ends,
   said occlusal member is generally triangular in shape in cross section between its first and second ends.

4. The apparatus of claim 1, wherein:
   said outer side of said gingival member gradually increases in width from its first and toward its second end,
   said gingival member is generally triangualr in shape in cross section between its first and second ends,
   said occlusal member is generally traingular in shape in cross section between its first and second ends.

5. The apparatus of claim 4, wherein:
   said first end of said gingival member is pointed.

6. The apparatus of claim 4, wherein:
   said occlusal member is generally L-shaped between its two ends.

7. The apparatus of claim 1, comprising:
   a hook means formed at said first end of said gingival member on its outer side,
   a V-shaped connecting means with inwardly facing pointed means at said second end of said gingival member,
   said two sides of said gingival member at its second end forming a trough which is separate from said V-shaped connecting means,
   a closed loop connecting means having an opening at said second end of said occlusal member,
   said two sides of said occlusal member at its second end forming a trough which is separated from said closed loop connecting means,
   a plurality of pairs of notches formed in said first end of said occlusal member, said second end of said occlusal member being adapted to be connected to said first end of said gingival member by locating said first end of said gingival member between said closed loop connecting means and said trough of said occlusal member with said hook means located within the opening of said closed loop connecting means, said first end of said occlusal member being adapted to be connected to said second end of said gingival member by locating said first end of said occlusal member within a portion of said trough and within said V-shaped connecting means of said gingival member with said pointed means located within one pair of said notches.

8. The apparatus of claim 4, comprising:

a hook means formed at said first end of said gingival member on its outer side, a V-shaped connecting means with inwardly facing pointed means at said second end of said gingival member, said two sides of said gingival member at its second end forming a trough which is separate from said V-shaped connecting means, a closed loop connecting means having an opening at said second end of said occlusal member, said two sides of said occlusal member at its second end forming a trough which is separated from said closed loop connecting means, a plurality of pairs of notches formed in said first end of said occlusal member, said second end of said occlusal member being adapted to be connected to said first end of said gingival member by locating said first end of said gingival member between said closed loop connecting means and said trough of said occlusal member with said hook means located within the opening of said closed loop connecting means, said first end of said occlusal member being adapted to be connected to said second end of said gingival member by locating said first end of said occlusal member within a portion of said trough and within said V-shaped connecting means of said gingival member with said pointed means located within one pair of said notches.

9. An apparatus for use in dental restoration, comprising:

a curved flexible member having a first end and a second end, said curved flexible member having a gingival portion and an occlusal protion, said occlusal portion extending from said first end to an intermediate position along the length of said member said gingival portion extending from about said intermediate position along the length of said member to said second end, said member having an outer side said member having two other sides which extend from opposite edges of said outer side to a pointed edge where they meet each other, means form connecting said first and second ends of said member together to form a closed loop wedge with said pointed edge defining a central opening, said member being adapted to be inserted partially through the gingival embrasure of two adjacent teeth, from its first end with its outer side facing the gum, to a position wherein its gingival position is within the gingival embrasure whereby the occlusal portion including its pointed edge may be fitted within the occlusal embrasure of the two adjacent teeth and said first and second ends connected together to form a closed loop wedge which fills the gingival, buccal, lingual, and occlusal embrasures between the two adjacent teeth.

10. The apparatus of claim 9, wherein:

said outer side of said member gradually increases in width from about said intermediate position toward its second end.

11. The apparatus of claim 9, wherein:

said member is generally triangular in shape in cross section between its first and second ends.

12. The apparatus of claim 9, wherein:

said outer side of said member gradually increases in width from about said intermediate position toward its second end, said member is generally triangular in shape in cross section between its first and second ends.

13. The apparatus of claim 12, wherein:

said member is C-shaped irom about said intermediate position along its length to said second end.

14. The apparatus of claim 12 wherein:

said member is generally L-shaped from about said intermediate position along its length to said first end.

15. The apparatus of claim 13, wherein:

said member is generally L-shaped from about said intermediate position along its length to said first end.

16. The apparatus of claim 12, wherein:

said first end of said member is pointed.

17. The apparatus of claim 9, comprising:

a plurality of pairs of notches formed in said first end of said member, and, a V-shaped connecting means with inwardly facing pointed means at said second end of said member, said two sides of said member at its second and forming a trough which is separate from said V-shaped connecting means, said first and second ends of said member being adapted to be connected together by locating said first end within a portion of said trough and within said V-shaped connecting means with said pointed means located within one pair of said notches.

18. The apparatus of claim 12, comprising:

a plurality of pairs of notches formed in said first end of said member, and, a V-shaped connecting means with inwardly facing pointed means at said second end of said member, said two sides of said member at its second and forming a trough which is separate from said V-shaped connecting means, said first and second ends of said member being adapted to be connected together by locating said first end within a portion of said trough and within said V-shaped connecting means with said pointed means located within one pair of said notches.

* * * * *